US 9,384,326 B2

(12) United States Patent
Kawagishi et al.

(10) Patent No.: US 9,384,326 B2
(45) Date of Patent: Jul. 5, 2016

(54) DIAGNOSIS SUPPORT APPARATUS, STORAGE MEDIUM STORING PROGRAM, AND METHOD FOR DEDUCING A DIAGNOSIS BASED ON INPUT FINDINGS

(75) Inventors: Masami Kawagishi, Yokohama (JP); Hidehiko Morinaga, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 0 days.

(21) Appl. No.: 13/212,454

(22) Filed: Aug. 18, 2011

(65) Prior Publication Data

US 2012/0054652 A1 Mar. 1, 2012

(30) Foreign Application Priority Data

Aug. 27, 2010 (JP) .................................. 2010-191212

(51) Int. Cl.
*G06F 19/00* (2011.01)
*G06Q 50/22* (2012.01)

(52) U.S. Cl.
CPC .............. *G06F 19/345* (2013.01); *G06Q 50/22* (2013.01)

(58) Field of Classification Search
CPC ...... G06F 19/345; G06F 9/4443; G06Q 50/22
USPC ........ 715/764; 600/408, 300; 382/128; 705/2
See application file for complete search history.

(56) References Cited

U.S. PATENT DOCUMENTS

| | | | |
|---|---|---|---|
| 5,697,373 A * | 12/1997 | Richards-Kortum | A61B 5/0071 356/301 |
| 7,458,936 B2 | 12/2008 | Zhou et al. | |
| 7,640,051 B2 | 12/2009 | Krishnan et al. | |
| 7,747,053 B2 | 6/2010 | Kadomura et al. | |
| 7,783,094 B2 | 8/2010 | Collins et al. | |
| 2002/0170565 A1* | 11/2002 | Walker .................. | G06F 19/322 702/19 |
| 2004/0091424 A1* | 5/2004 | Asano et al. .................... | 424/9.1 |
| 2005/0181361 A1* | 8/2005 | Kim .................................. | 435/6 |
| 2007/0022025 A1* | 1/2007 | Litman et al. .................... | 705/30 |
| 2011/0257988 A1* | 10/2011 | Denekamp et al. ............... | 705/2 |

FOREIGN PATENT DOCUMENTS

| | | |
|---|---|---|
| CN | 1522420 A | 8/2004 |
| CN | 1836240 A | 9/2006 |
| JP | 10-177605 A | 6/1998 |
| JP | 2001-312558 A | 11/2001 |
| JP | 2004-029927 A | 1/2004 |
| JP | 2004-288047 A | 10/2004 |
| WO | 2010035161 A1 | 4/2010 |

OTHER PUBLICATIONS

Robert M Nishikawa,"Computer-Assisted Detection and Diagnosis",Encyclopedia of Medical Devices and Instrumentation, Second Edition, 2006, pp. 284-306.

* cited by examiner

*Primary Examiner* — Li Sun
(74) *Attorney, Agent, or Firm* — Canon USA, Inc. IP Division

(57) ABSTRACT

A diagnosis support apparatus includes a display control unit configured to display an input GUI which receives input of a plurality of findings regarding a subject, a deducing unit configured to deduce a diagnosis of the subject on the basis of the findings input through the input GUI, and a determining unit configured to determine whether one of the plurality of input findings supports the deduction or not. In this case the display control unit changes the display form of the input GUI which receives input of the determined finding in accordance with the determination result.

23 Claims, 8 Drawing Sheets

FIG. 2

| j | Ij (NAME OF FINDING) | jk | Sjk (NAME OF CONDITION) |
|---|---|---|---|
| 1 | FORM | 11 | GLOBULAR |
| | | 12 | LOBULATED |
| | | 13 | IRREGULAR |
| 2 | CUT | 21 | STRONG |
| | | 22 | MEDIUM |
| | | 23 | WEAK |
| | | 24 | NONE |
| 3 | RADIAL | 31 | STRONG |
| | | 32 | MEDIUM |
| | | 33 | WEAK |
| | | 34 | NONE |
| ... | | | |
| m | INVOLUTION (BLOOD VESSEL) | m1 | YES |
| | | m2 | SUSPECTED |
| | | m3 | NO |
| ... | | | |
| n | KL-6 | n1 | NORMAL VALUE |
| | | n2 | ABNORMAL VALUE |

FIG. 6

| j | k | Ij (NAME OF FINDING) | Sjk (NAME OF CONDITION) | C(D1\|Sjk) | C(D2\|Sjk) | C(D3\|Sjk) |
|---|---|---|---|---|---|---|
| 1 | 1 | FORM | GLOBULAR | −0.15 | 0.10 | 0.05 |
| 3 | 3 | RADIAL | WEAK | −0.10 | 0.03 | 0.07 |
| ... | | | ... | | | |
| m | 3 | INVOLUTION (BLOOD VESSEL) | NO | −0.12 | 0.25 | −0.13 |
| ... | | | | | | |
| n | 2 | KL-6 | ABNORMAL VALUE | −0.15 | −0.15 | 0.30 |

DIAGNOSIS SUPPORT APPARATUS, STORAGE MEDIUM STORING PROGRAM, AND METHOD FOR DEDUCING A DIAGNOSIS BASED ON INPUT FINDINGS

BACKGROUND OF THE INVENTION

1. Field of the Invention

The present invention relates to diagnosis support apparatuses and diagnosis support systems which provide information that supports a diagnosis, information processing apparatus control methods and computer-readable memories storing a program for performing information processing.

2. Description of the Related Art

In medical fields, image diagnosis have been performed in which a doctor examines medical images acquired by an imaging apparatus such as an MRI and/or an X-ray CT for a diagnosis. In image diagnosis, a diagnoser synthetically determines finding or measured values acquired from an image and identifies a symptom of a lesion present on the image. In other industrial fields than medical fields, a diagnoser examines an image or an actual apparatus, synthetically determines a plurality of measured values and/or findings and thus diagnoses a cause of a failure, for example.

In order to support those diagnoses, diagnosis support apparatuses have been developed for deducing a disease name on the basis of findings from a image or a subject input by a diagnoser. Japanese Patent Laid-Open No. 2004-29927 discloses an art which draws an inference from finding by a diagnoser, a major complaint by a patient, an examination result and so on to deduce a disease. U.S. Pat. No. 7,747,053 discloses an art which displays a marker for an abnormal shadow candidate and information which has been used for determining an abnormality over a medical image and presents a reason for detection of an abnormal shadow candidate.

An apparatus which deducts a diagnosis from a finding input by a diagnoser may require correction of the input finding if the finding on which the deduction has been based is wrong. Accordingly, the present invention allows a user to easily correct a finding on which the deduction of a disease name is based.

SUMMARY OF THE INVENTION

Accordingly, a diagnosis support apparatus according to an aspect of the present invention includes a display control unit configured to display an input GUI which receives input of a plurality of findings regarding a subject, a deducing unit configured to deduce a diagnosis of the subject on the basis of the findings input through the input GUI, and a determining unit configured to determine whether one of the plurality of the input findings supports the deduction or not. In this case the display control unit changes the display form of the input GUI which receives input of the determined finding in accordance with the determination result.

Further features of the present invention will become apparent from the following description of exemplary embodiments with reference to the attached drawings.

BRIEF DESCRIPTION OF THE DRAWINGS

FIG. 2 illustrates a correspondence table between names of findings and corresponding names of conditions.

FIG. 6 illustrates findings and corresponding contribution ratios.

FIG. 8A illustrates a hardware configuration of the diagnosis support system implemented by hardware and software. FIG. 8B illustrates a configuration of the diagnosis support system implemented by hardware and software.

DESCRIPTION OF THE EMBODIMENTS

With reference to drawings, forms for embodying the present invention will be described on the basis of the following embodiments below.

A diagnosis support system according to a first embodiment deduces the type of abnormality (diagnosis) of an abnormal shadow on the basis of medical information such as a finding on a subject. Among medical information used for the deduction, medical information that affirms that the subject may be matched with the diagnosis and medical information that denies it are acquired. The fact is displayed on a finding input screen.

Figure 1:
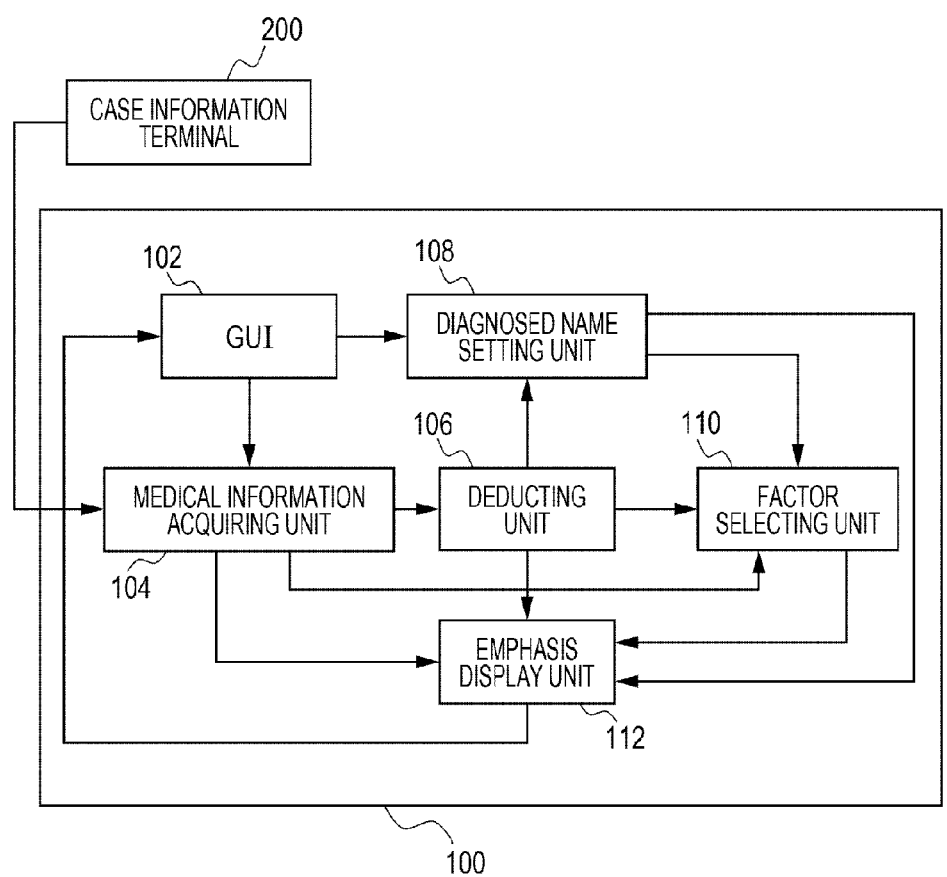
FIG. 1 illustrates a configuration of a diagnosis support system.

FIG. 1 illustrates a configuration of a diagnosis support system 1. A diagnosis support apparatus 100 is connected to a case information terminal 200.

The case information terminal 200 acquires information on an abnormal shadow on the lung (such as medical image and information on an electronic medical record) from a server, not illustrated. Alternatively, an external storage such as an FDD, an HDD, a CD drive, a DVD drive, an MO drive, and a ZIP drive may be connected thereto, and the data may be acquired from the drive. The information is displayed on a monitor in a form that is interpretable by a user (doctor).

The case information terminal 200 in accordance with a request by a user further transmits associated data (such as a representative image and clinical data such as a tumor marker value) on the abnormal shadow on the lung to the diagnosis support apparatus 100 via a LAN, for example.

The diagnosis support apparatus 100 includes the following components:

A GUI (Graphical User Interface)102 includes a monitor, not illustrated. The monitor displays clinical data (such as a representative image and clinical data such as a tumor marker value) on the abnormal shadow on the lung. The GUI 102 includes an input GUI (including the name of a finding and a selection GUI for the corresponding state) for inputting a finding from interpretation of the image on the abnormal shadow. A user may use a mouse and/or a keyboard to input a finding. The GUI 102 further includes an input GUI (including a diagnosis and a selection GUI for the corresponding impression) for inputting an impression regarding the diagnosis. A user may use a mouse and/or a keyboard to input an impression through the input GUI. The input finding and impression is output to a medical information acquiring unit 104. The term, impression, here refers to a predicted diagnosis to be input along with a finding by a user of the diagnosis support apparatus 100. The input impression is output to the diagnosis setting unit 108. The CPU, not illustrated, within the diagnosis support apparatus 100 may function as a unit which creates an image to be displayed on a monitor and a control unit which performs display control over the monitor.

The medical information acquiring unit 104 acquires medical information (input information) input to the diagnosis support apparatus 100. The medical information or input information may include a finding from interpretation of the image on an abnormal shadow on the lung input through the GUI 102. The case medical information or input information may further include a part of associated data (such as clinical data such as a tumor marker value) transmitted from the information terminal 200. The medical information is not limited thereto. All of the following diagnoses, inputable findings, and tumor marker values will be given only for illustration of step S4000 of processing by the medical diagnosis support apparatus 100. The medical information acquiring unit 104 outputs the input information to a deducting unit 106, a factor selecting unit 110, and an emphasis display unit 112.

The deducting unit 106 deduces the diagnosis of a subject on the basis of the input information. The deducting unit 106 performs deduction regarding an abnormal shadow on the lung of the subject and calculates the probability (deduction result) that the abnormal shadow is matched with diagnoses. The deducting unit 106 may function as a unit which determines whether input information affirms or denies the deduction. According to this embodiment, the deducting unit 106 determines whether input information affirms or denies that the subject is matched with a diagnosis or the degree (contribution ratio). The contribution ratio of input information that affirms that the subject is matched with the diagnosis is a positive value. On the other hand, the contribution ratio of input information that denies it is a negative value.

The acquired deduction result is output to a diagnosis setting unit 108 and an emphasis display unit 112, and the contribution ratio is output to the factor selecting unit 110 and emphasis display unit 112.

The diagnosis setting unit 108 sets the diagnosis having the highest probability as a subject diagnosis on the basis of the deduction result acquired by the deducting unit 106. The set subject diagnosis is output to the factor selecting unit 110 and emphasis display unit 112. The pair of the deducting unit 106 and the diagnosis setting unit 108 functions as a unit which deduces a diagnosis.

The factor selecting unit 110 selects from input information input information (positive information) having the highest degree of affirmation of the subject diagnosis set by the diagnosis setting unit 108 and input information (negative information) having the highest degree of denial. The details of the selection processing will be described below. The selection result is output to the emphasis display unit 112.

The emphasis display unit 112 performs display (emphasis display) which emphasizes an input GUI of an impression regarding the corresponding diagnosis on the basis of the subject diagnosis set by the diagnosis setting unit 108.

If the input information selected by the factor selecting unit 110 is a finding acquired through the GUI 102, the emphasis display unit 112 performs display (emphasis display) which emphasizes the input GUI of the finding on the basis of the contribution ratio acquired by the deducting unit 106. If the selected input information is a part of the associated data, the emphasis display unit 112 displays a display unit of the associated data on the GUI 102 with emphasis on the basis of the contribution ratio acquired by the deducting unit 106.

Next, with reference to FIG. 2, a management method for medical information in the diagnosis support system 1 will be described. A finding from interpretation of an image and a tumor marker value which is an example of a measured value is referred by Ij (j=1 to n), and it is assumed that n types of findings and tumor marker values I1 to In will be handled. The k states that Ij may have will be referred by Sjk. The range of k may vary in accordance with Ij. According to this embodiment, for example, the findings and tumor marker values as illustrated in FIG. 2 may be input or acquired, and the findings and tumor marker values may have the states as illustrated. For example, the "form" for I1 exhibits a form of an abnormal shadow and may have three states of S11 "globular", S12 "lobulated", and S13 "irregular". The "cut" for I2 describes the degree of cut of an abnormal shadow. The "involution (blood vessel)" for Im describes the presence of an involution of a blood vessel in an abnormal shadow. The "KL-6" for In describes whether Sialylated carbohydrate antigen KL-6 in a serum, which is used as a tumor marker for interstitial pneumonia, falls within reference values (equal to or lower than 500 U/ml) or not.

A set of Sjks is referred by E. However, a plurality of states Sjks of one Ij do not exist simultaneously in one E. For example, if I1 has S11, S12, and S13 and I2 has S21, S22, S23, and S24, E={S11, S21} may be possible while E={S11, S12} is impossible. This is because one finding and tumor marker value may have only one state. A diagnosis will be referred by a symbol D in the following descriptions. According to this embodiment, the diagnosis may have three values of primary lung cancer, cancer spread to lung, and others, which will be referred by D1, D2, and D3, respectively. The deduced probability of a diagnosis Dr (r=1, 2, 3) with a set E given as input information will be referred by P(Dr|E). The contribution ratio of an element Sjk of E for the diagnosis Dr will be referred by C(Dr|Sjk).

Figure 3:
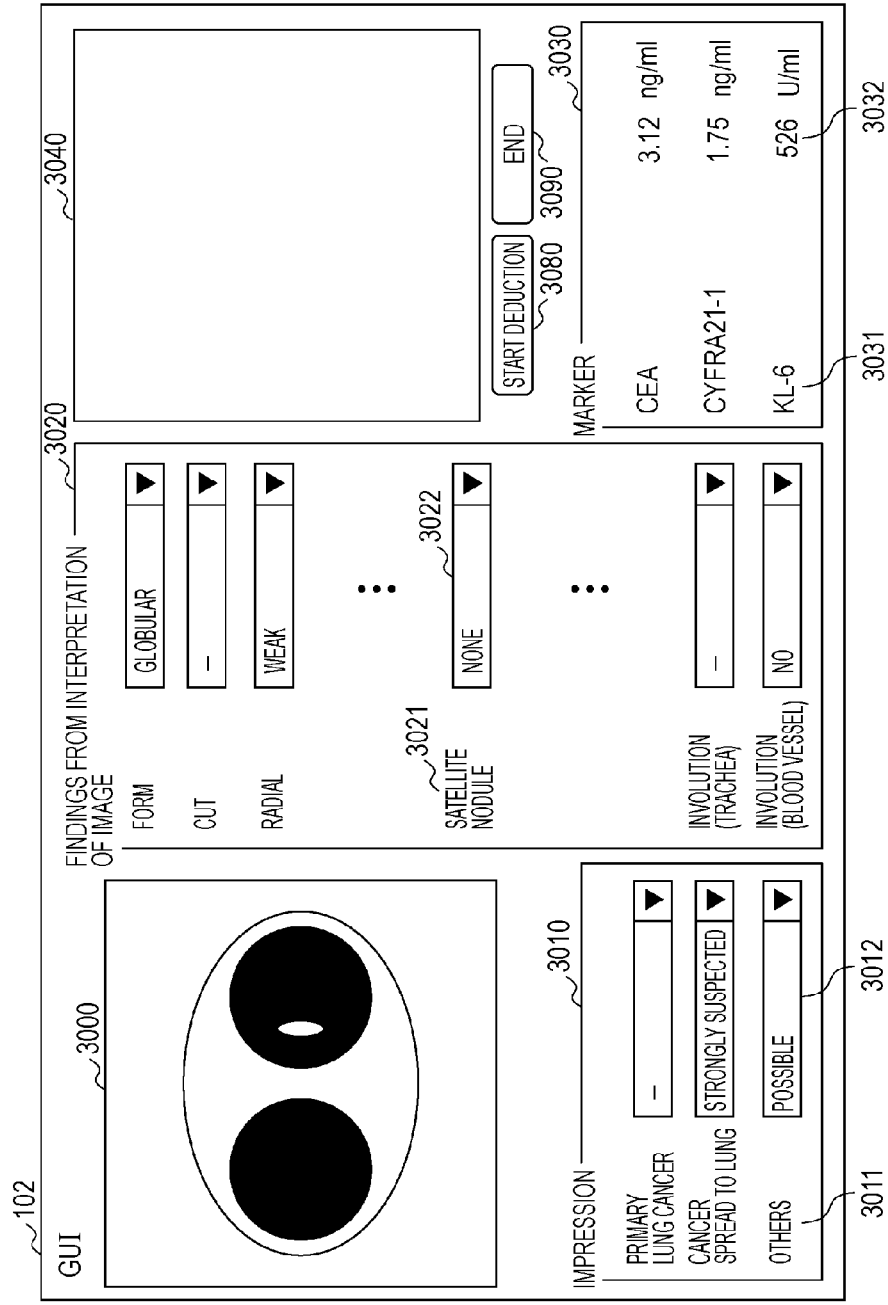
FIG. 3 illustrates an example of a GUI.

FIG. 3 illustrates a display example of the GUI 102 according to this embodiment. The display of the GUI 102 is generated and controlled by a CPU, not illustrated. A representative image 3000 of an abnormal shadow on the lung is displayed here. A region 3030 which displays the measured value of a tumor marker displays a tumor marker name 3031 and a measured value 3032 corresponding thereto. A region 3020 and a region 3010 are further displayed. The region 3020 is used by a user to input a finding from interpretation of image 3000 on an abnormal shadow. The region 3010 is used by a user for inputting an impression. The region 3020 further displays input GUIs for findings including a pair of the name of finding 3021 and a pull-down menu 3022 from which a name of condition is selectable by a user. The name of finding 3021 displays a list including "form" and "cut". For example, the pull-down menu 3022 for the name of finding 3021 which is "form" includes "globular", "lobulated" and "irregular".

The region 3010 displays an input GUI for an impression regarding a diagnosis. The input GUI for an impression displays a pair of a diagnosis 3011 and a pull-down menu 3012 from which an impression is selectable by a user. For the diagnosis 3011, "primary lung cancer", "cancer spread to lung" and "others" may be displayed. The pull-down menu 3012 may display representations indicating possibilities of diagnoses such as "certain", "strongly suspected", "suspected", "possible", and "do not deny the possibility".

A user may use the GUI 102 to input a finding from interpretation of the image 3000 and an impression and then push a "deduction start" button 3080 or "end" button 3090. If the "deduction start" button 3080 is pushed on the GUI 102, the deducting unit 106 is instructed to start deduction processing. As a deduction result, the region 3040 displays the calculated probabilities and diagnoses in association. The display will be described later.

The GUI 102 displays an image of a subject, an input GUI for a finding, a GUI for an impression, a measured value for a tumor marker, a button 3080 for instructing the deduction, and a deduction result on one screen. In this way, whether the input finding is right or not may be checked by checking the image, measured value and deduction result. If not, the wrong finding may be corrected through the input GUI. After that, the button 3080 for instructing the deduction may be pushed to instruct the deduction again to display the corrected result on one screen. This allows efficient image diagnosis by using the diagnosis support apparatus.

The image, measured value and finding on which a diagnosis is based objectively, an impression which is a prediction including the subjectivity of a doctor, a diagnosis based on the deduction by the diagnosis support apparatus may be checked on one screen. This may support the efficient check on details of a diagnosis in medical scenes where efficiency and advanced accuracy may be required.

Next, with reference to the flowchart in FIG. 4, a processing flow by the diagnosis support apparatus 100 will be described.

In step S4000, the diagnosis support apparatus 100 inputs associated data on an abnormal shadow on the lung from the case information terminal 200.

In step S4005, the diagnosis support apparatus 100 displays the GUI 102 on a monitor and acquires a finding from interpretation of the image and an impression. A user here may operate a mouse or keyboard, not illustrated, to select a finding and an impression from pull-down menus. The diagnosis support apparatus 100 interprets an operation signal from the mouse or keyboard in association with the information on the GUI 102. The finding and impression selected on the GUI 102 are thus input to the diagnosis support apparatus 100.

In step S4006, whether the end button 3090 has been pushed or not is determined. If not, the processing moves to step S4007.

In step S4007, whether any change on a finding or impression GUI 102 has been input or not is determined. If not, the processing moves to step S4008.

In step S4008, whether the process/diagnosis has been changed on the GUI 1102 or not is determined. Because the process/diagnosis is changed by selecting one of the deduction results displayed on the region 3040, the change is not allowed before the deduction processing on the diagnosis is performed in and after step S4010. The process/diagnosis has not been changed, the processing moves to step S4009.

In step S4009, whether the "deduction start" button 3080 has been pushed or not is determined. If not, the processing moves to step S4006. In this way, if nothing is input by a user, the determining processing from step S4006 to step S4009 is looped, and the diagnosis support apparatus 100 has a standby state for an input.

In step S4009, the diagnosis support apparatus 100 determines whether the "deduction start" button 3080 on the GUI 102 has been pushed by a user operation or not. If so, the processing moves to step S4010 where deduction processing by the deducting unit 106 is performed.

In step S4010, the medical information acquiring unit 104 acquires input information for deduction. In this case, the finding acquired in step S4005 and the tumor marker value which is a part of the associated data acquired in step S4000 are acquired as input information E regarding the abnormal shadow on the lung. If serial tumor marker values are input, a predetermined conversion rule may be used to convert them to a state. For example, of the acquired tumor marker value In "KL-6" is 526 U/ml, the value is converted to In "KL-6":Sn 2 "abnormal value" since it is higher than a reference value.

In step S4020, the deducting unit 106 calculates the probabilities that the abnormal shadow is matched with diagnoses (deduction result) on the basis of the input information E regarding the abnormal shadow on the lung acquired in step S4010. The deducting unit 106 further calculates contribution ratios of the element Sjk included in the input information E to diagnoses.

Various existing deduction methods such as Bayesian network, neural network, and support vector machine may be applied to the deduction. According to this embodiment, Bayesian network is applied as the deduction unit. Bayesian network is a deduction model using conditional probabilities and allows acquisition of deducted probabilities of diagnoses if input information is input (the probability that the case is matched with the diagnoses, which also be called a posterior probability). According to this embodiment, the probabilities that the abnormal shadow is matched with diagnoses D1, D2, and D3 are acquired.

According to this embodiment, the contribution ratio of the state Sjk is acquired by using the differences between probabilities of diagnoses if nothing is input (also called a priori probability) and the deducted probabilities if Sjk is only input. For example, the contribution ratio C of Sjk to a diagnosis Dr (Dr|Sjk) is calculated by Expression (1) below where P(Dr) is the priori probability of Dr.

$$C(D_r|S_{jk}) = P(D_r|S_{jk}) - P(D_r) \quad (1)$$

The priori probability may be the proportion of the number of cases recorded in the case information terminal 200. For example, if the proportion of the number of cases relating to the abnormal shadow on the lung recorded in the case information terminal 200 is "primary lung cancer": 20%, "cancer spread to lung": 50%, and "others": 30%, these values are used as priori probabilities of diagnoses. Assuming that the number of cases recorded in case information terminal 200 is sufficiently high, the priori probabilities exhibit probabilities that the abnormal shadow on the lung correspond to the diagnoses in general. If the contribution ratio of the state Sjk calculated on the basis of the priori probability is positive values, it may be said that the state Sjk is matched with the diagnosis is affirmed or supported. Conversely, if the contribution ratio is a negative value, it means that the probability that the state Sjk is matched with the diagnosis is lower than a general probability. Thus, it may be said that the state Sjk denies the diagnosis or is contrary to the correspondence to the diagnosis.

In this way, the deducting unit 106 determines whether input information affirms or denies the deduction by the deducting unit 106 on the basis of the sign (positive or negative) of the contribution ratio. Each of the input information is associated with the sign information of the contribution ratio as the determination result. The absolute value of the contribution ratio indicating the degree of the affirmation or denial is associated therewith as the determination result. Alternatively, the value of the contribution ratio may be associated therewith as the determination result.

Alternatively, the contribution ratios may be determined by using the difference between the probability calculated by using the input information E by the deducting unit 106 and the probability calculated from the input information E excluding the state Sjk. The thus calculated contribution ratio of the state Sjk is a value in consideration of the correlation with a state included in the input information E excluding the Sjk. In other words, the contribution having higher correlations with a plurality of states is an advantageous index.

In step S4030, the diagnosis setting unit 108 sets one diagnosis as the subject diagnosis on the basis of the deduction result acquired in step S4020. According to this embodiment, the diagnosis having the highest deduced probability among diagnoses is set as the subject diagnosis. For example, if the deduced probabilities of D1, D2, and D3 are 25%, 45%, and 30%, respectively, D2 is set as the subject diagnosis. In this way, the deducting unit 106 and diagnosis setting unit 108 deduce a diagnosis.

In step S4040, the factor selecting unit 110 selects positive information and negative information on the subject diagnosis set in step S4030 from the input information acquired in step S4010 on the basis of the acquired contribution ratio. According to this embodiment, input information which has a maximum contribution ratio in the positive values is selected as the positive information. The input information which has a minimum contribution ratio in the negative values is selected as the negative information. For example, if the subject diagnosis is D2 and the contribution ratios of the input information are as illustrated in the table in FIG. 5, Im "involution (blood vessel)":Sm 3 "none" is selected as the positive information, and In "KL-6":Sn 2 "abnormal value" is selected as the negative information.

In step S4050, the emphasis display unit 112 displays the input GUI of an impression relating to the corresponding diagnosis with emphasis on the basis of the subject diagnosis set in step S4030. If the input information selected in step S4040 is a finding from interpretation of the image 3000 acquired through the GUI 102, the input GUI of the finding is displayed in a display form according to the contribution ratio acquired by the deducting unit 106. According to this embodiment, the pull-down menus and text information corresponding to the subject diagnosis, positive information, and negative information are provided within colored frames.

The diagnosis support apparatus 100 terminates the display of the "deduction start" button 3080.

Figure 4:
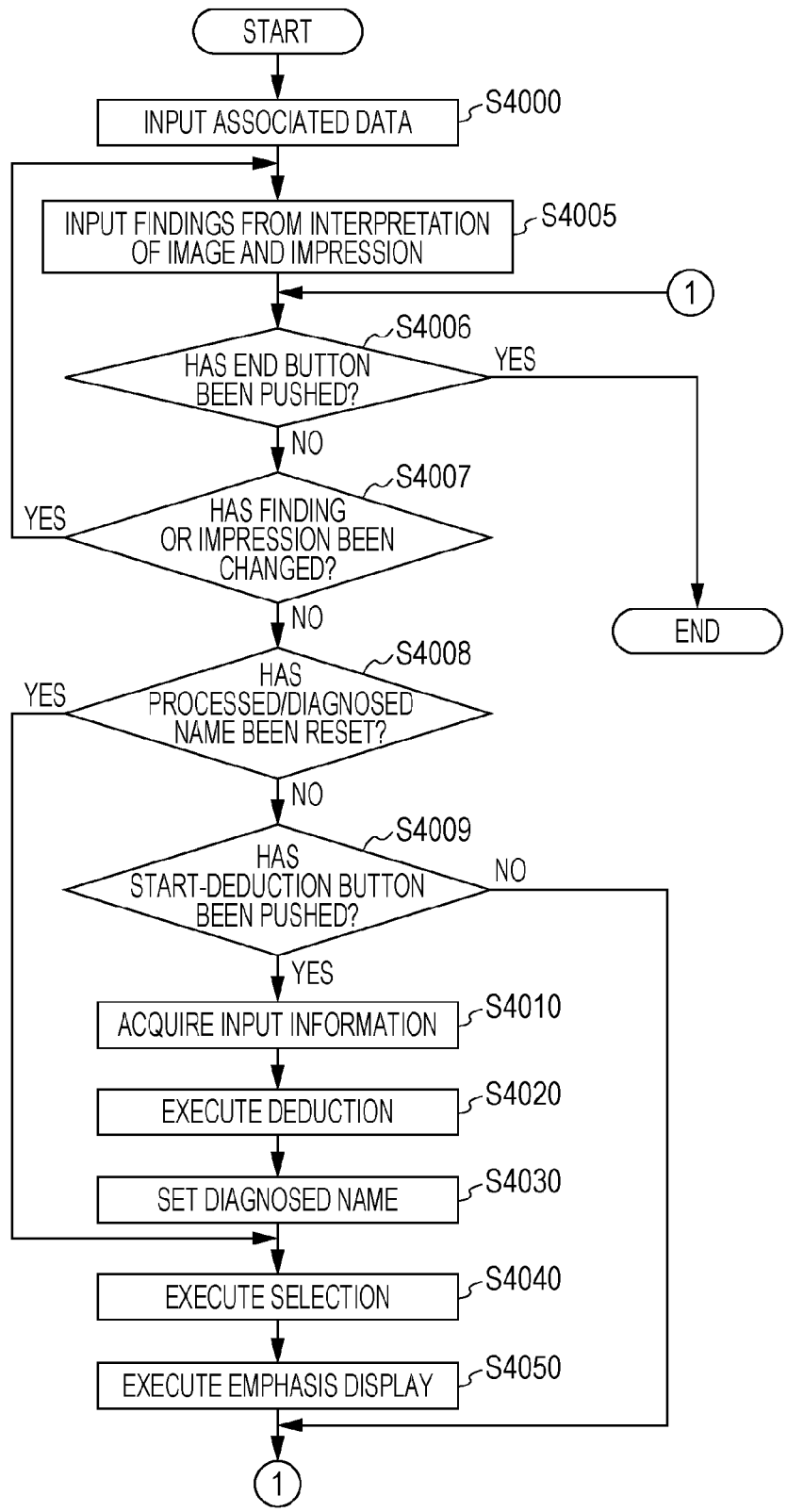
FIG. 4 is a flowchart illustrating a processing routine by the diagnosis support apparatus.
Figure 5:
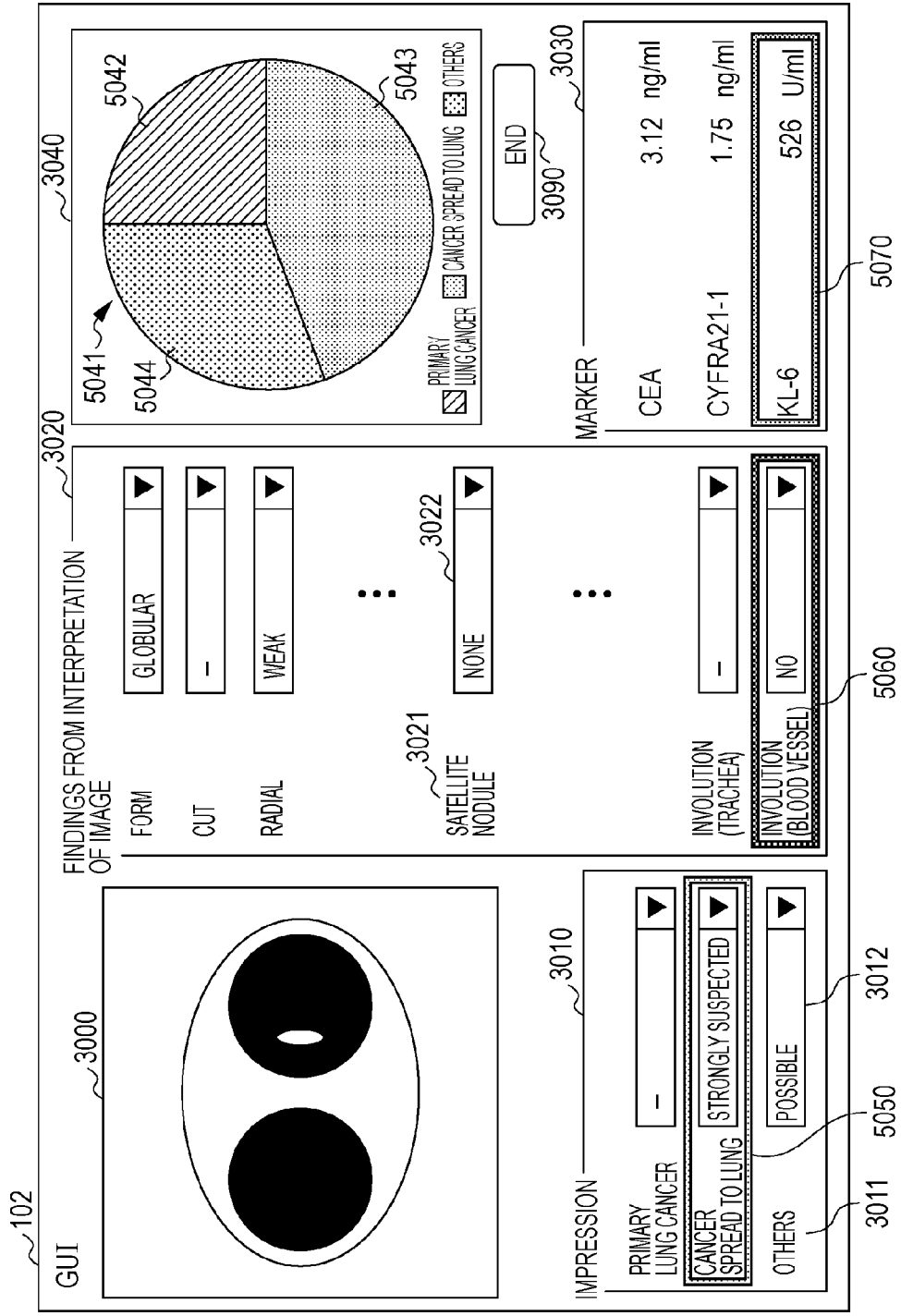
FIG. 5 illustrates an example of emphasis display on the GUI.

FIG. 5 illustrates an example of the emphasis display on the GUI 102 in step S4050. The GUI 102 is caused to display, in addition to the display in FIG. 4, the result of the deduction acquired in step S4020 in a deduction result display region 3040. In the example in FIG. 5, a deduction result pie graph display 5041 is displayed in the deduction result display region 3040. The deduction result pie graph display 5041 includes a pie graph display 5042 for the deduced probability for the primary lung cancer, a pie graph display 5043 for the deduced probability for the cancer spread to lung, and a pie graph display 5044 for other deduced probabilities. A frame surrounding an input GUI for an impression regarding the subject diagnosis is displayed in the region 3010. If the subject diagnosis is D2, the input GUI for an impression regarding the "cancer spread to lung" is surrounded by a frame 5050 with emphasis as illustrated in FIG. 5.

A frame surrounding the positive information and a frame surrounding the negative information are displayed in the region 3020 or region 3030. For example, if Im "involution (blood vessel)":Sm 3 "none" which is a finding from interpretation of the image 3000 is selected as the positive information, the input GUI for the name of finding "involution (blood vessel)" is surrounded by a blue frame 5060 indicating affirmation, as illustrated in FIG. 5. The parts within the frames may blink for emphasis. This display exhibits that the finding that the name of finding "involution (blood vessel)" is matched with "Sm 3 "none"" is determined as the information that affirms the deduction.

If the tumor marker, In "KL-6":Sn 2 "abnormal value", is selected as the negative information, the display area of the tumor marker "KL-6" is surrounded by a red frame 5070. The area within the frame blinks for emphasis.

In this way, the display of the positive information and negative information is given to the GUI 102, and the display form is changed. It may support intuitive check by a user. Since the base for the deduction result of a diagnosis may be intuitively grasped, the diagnoser easily determines the reliability of the deduction result. The display of affirmation and denial is given to a pull-down menu for inputting a finding so that a user may easily find the position to be corrected if the finding is wrong and correct it. This may increase the accuracy and efficiency of the diagnosis.

Alternatively, for example, a display unit of findings or measured values on the GUI 102 may be displayed with emphasis in a form according to the contribution ratio acquired by the deducting unit 106. The emphasis display unit 112 causes the red frame or blue frame given to the input GUI to blink at a time interval according to the absolute value of the contribution ratio. According to this embodiment, the blinking interval has three steps. In other words, if the absolute value of the contribution ratio is equal to or higher than 20, the blinking interval is short (10 ms). If it is equal to or higher than 10 and lower than 20, the blinking interval is medium (100 ms). If it is lower than 10, the blinking interval is long (500 ms). For example, if the absolute value of the contribution ratio of Im "involution (blood vessel)":Sm 3 "none" is equal to 25 and the absolute value of the contribution ratio of In "KL-6":Sn 2 "abnormal value" is equal to 15, the blue frame 5060 indicating the affirmation blinks at the short intervals. The red frame 5070 indicating the denial blinks at the medium intervals. This allows intuitive understanding of the degree of affirmation or denial of input information on the screen.

According to another display example, the positive/negative of the contribution ratios of all findings may be displayed in the finding input GUI. By using the contribution ratios of the finding calculated in the deducting unit 106, the emphasis display unit 112 displays the name of a finding with a positive contribution ratio and the pull-down menu therefor in the input GUI within a blue frame. The name of a finding with a negative contribution ratio and a pull-down menu therefore may be displayed within a red frame. This allows a user to easily check and correct the contribution ratios of findings on the display of the input GUI. The emphasis display unit 112 further causes the areas within the frames at the time intervals according to the contribution ratios. This allows intuitive grasp of a finding having a large influence and may prompt correction.

According to another display example, among findings, a finding having a positive and highest contribution ratio and a finding having a negative and lowest contribution ratio may be displayed with emphasis. In order to do so, the factor selecting unit 110 selects, from finding information, the finding that affirms the most highly affirmed diagnosis and the finding that denies it as the positive information and the negative information. Alternatively, both of the information having the highest contribution ratio in all input information E and the finding having the highest contribution ratio in the findings may be selected as the positive information. Similarly to the negative information, the information having the highest degree of denial in all input information E and the finding having the highest degree of denial in the findings may be selected as the negative information. This processing selects the positive information and negative information for a finding. The emphasis display unit 112 displays the selected positive information and negative information with emphasis. This allows a user to easily check whether the input of the finding is wrong or not.

The case where it is determined in step S4008 that the subject diagnosis has been changed (Yes in S4008) will be described. Step S4008 is processing that determines the reset of a diagnosis and is performed after a deduction result is calculated by the deducting unit 106 once.

If the pie graph display 5041 for a deduction result on the GUI 102 is clicked with a mouse, the diagnosis displayed at the clocked position may be selected and be reset as the subject diagnosis. If the pie graph display 5042 for the deduced probability for the primary lung cancer is clicked with a mouse, the diagnosis setting unit 108 resets the subject diagnosis to the primary lung cancer. In step S4040, the factor selecting unit 110 selects the positive information and negative information on the reset diagnosis from the input information E. In step S4050 after that, the emphasis display unit 112 displays the input GUI with emphasis. For example, if the contribution ratios of input information have the values as illustrated in FIG. 6, no input information have positive contribution ratios. Therefore, positive information is not selected, and I3 "radial": S33 "weak" is selected as the negative information. Then, the processing in step S4050 is performed where the input GUI for an impression regarding "primary lung cancer" is surrounded by the frame 5050 for emphasis display in the region 3010. In the region 3020, the input GUI for the name of finding "radial" is surrounded by the red frame 5070 indicating the denial and blinks for emphasis display. The display is then shifted to the input standby state again.

This may also display the positive information and negative information on a diagnosis set by a user. For example, if it is determined that the probability for "primary lung cancer" and the probability for "cancer spread to lung" are close, not only "primary lung cancer" having the highest probability but also "cancer spread to lung" may be required to check in detail. In order to address such a case, affirming information and denying information may be displayed for a diagnosis excluding the deduced diagnosis even after the deduction result is checked once.

In step S4007, the diagnosis support apparatus 100 determines whether any finding or impression has been changed or not. From the input GUI for a finding in the region 3020 and/or the input GUI for an impression regarding a diagnosis in the region 3010, whether data in the regions have been changed or not is determined. If it is determined that some finding or impression has been changed, the processing moves to step S4005. If some finding has been corrected, it is determined that the necessity for executing new deduction has arisen. The button 3080 which instructs the deduction start is displayed again. This allows a user to deduce a diagnosis again on the basis of the corrected finding.

If it is determined that the "end" button 5090 has been pushed, the processing ends.

The aforementioned processing allows a user to check the positive information and negative information to review his or her mistake regarding the diagnosis. In some cases, a user may input by mistake, and the input may generate affirmative and/or negative information for a subject name. The user's input error may be examined by checking the presented information. The information are displayed in different forms on the input GUI, allowing intuitive grasp of the part on which the determination on the deduction result by the medical diagnosis support apparatus is based. This further allows easy determination of the reliability of the medical diagnosis support apparatus.

A second embodiment applies a radio button as the input GUI for a finding. The result of deduction is displayed with a bar graph. The emphasis display of the positive information and negative information is implemented with an input GUI surrounded by an icon indicating a diagnosis, an icon indicating the positive information, and an icon indicating the negative information. The emphasis display may further include changes in brightness of the icons according to the contribution ratios. Because the configuration of the diagnosis support system according to this embodiment is similar to the diagnosis support system 1 according to the first embodiment, the corresponding description will be omitted. However, the form of the emphasis display by the display and emphasis display unit 112 in the GUI 102 differs. It is illustrated in FIG. 7.

Figure 7:
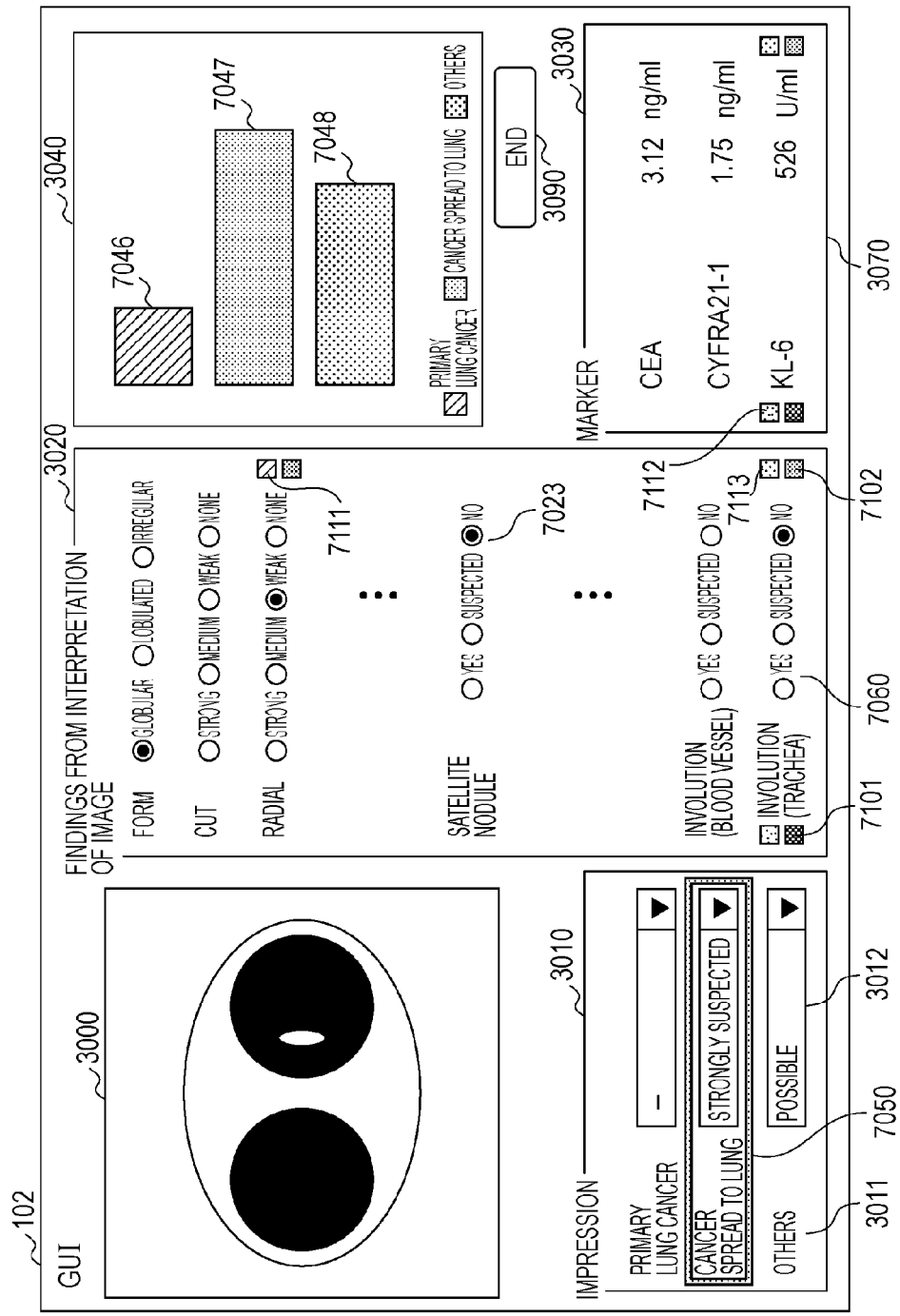
FIG. 7 illustrates another example of the emphasis display on the GUI.

FIG. 7 illustrates another example of the emphasis display in the GUI 102 according to this embodiment. The description on the parts described with reference to FIG. 3 and FIG. 5 will be omitted. In the region 3020, a pair of a name of finding 7021 and a radio button 7023 being an input GUI for a finding is displayed. With the radio button 7023, the corresponding name of condition is selectable by a user. In the region 3040, a bar graph display 7046 for a deduced probability for a cancer, a bar graph display 7047 for a deduced probability for a cancer spread to lung, and a bar graph display 7048 for other deduced probabilities are displayed.

According to the emphasis display example, the positive information and negative information regarding all diagnoses are displayed. More specifically, the icon 7101 indicating the positive information and an icon indicating a diagnosis are displayed on the right-hand side of the name of finding 7021. The icon indicating a diagnosis may be one of an icon 7111 indicating the primary lung cancer, an icon 7112 indicating the cancer spread to lung and an icon 7113 indicating others. An icon 7102 indicating the negative information and an icon indicating a diagnosis are further displayed on the right-hand side of the name of finding 7021. These icons have different brightnesses in accordance with their contribution ratios. For example, if the absolute value of the contribution ratio is high, the corresponding icon is displayed brighter. Otherwise, it is displayed darker.

These emphasis displays are given for illustration purpose only, and the present invention is not limited thereto. For example, a list box may be used as the finding input GUI. Various types of input GUI may be mixed. Instead of the text display of the tumor marker value which is a measured value, the display may be implemented by an input GUI. In this case, the initial value is desirably set with the value acquired from the associated data. Those values may be corrected by a user. The deduction result may be displayed with text including correspondence between a diagnosis and a probability.

Figure 8A:
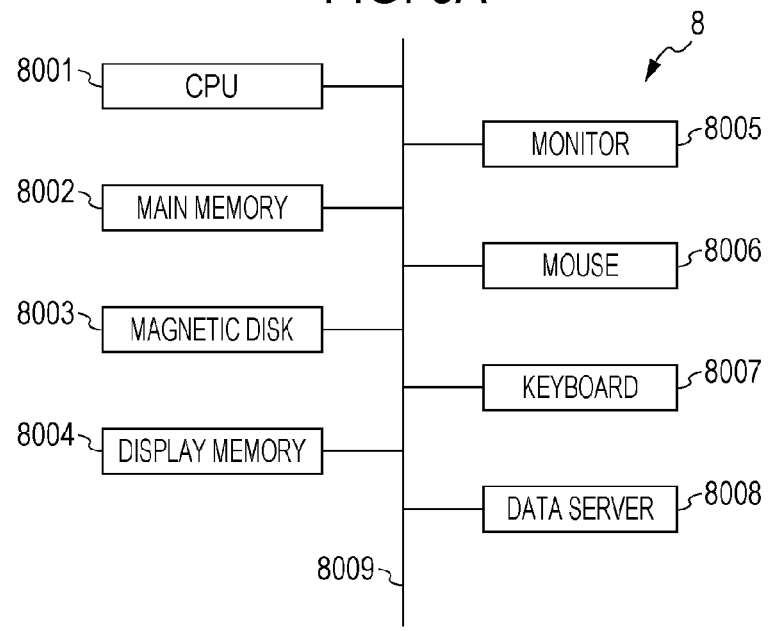
FIGS. 8A and 8B illustrate a configuration of another diagnosis support system 8.
Figure 8B:
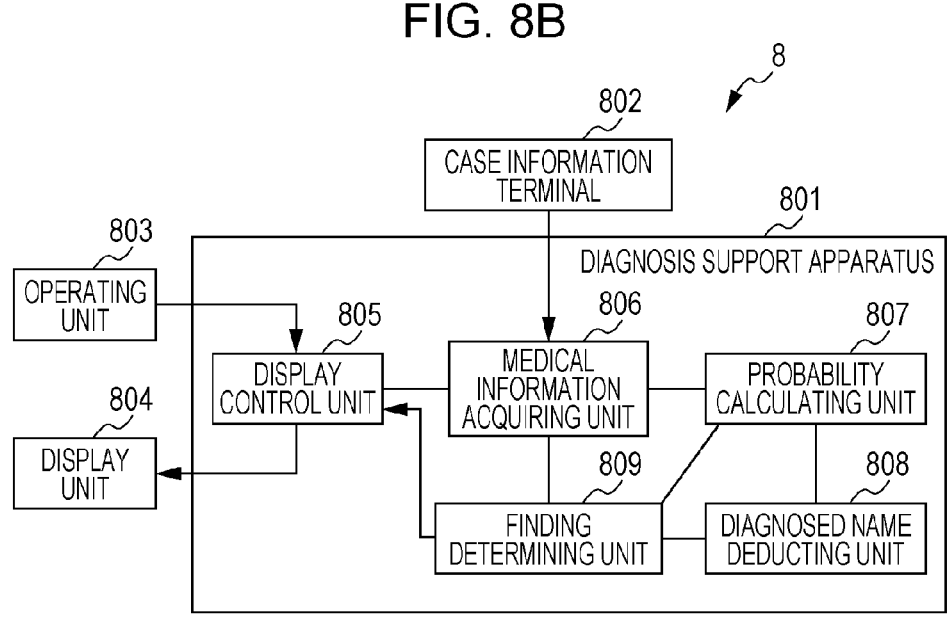

According to a third embodiment, the present invention is implemented by computer hardware and software. FIG. 8A illustrates a hardware configuration of a diagnosis support system 8. FIG. 8B illustrates functions implemented by software and hardware of the diagnosis support system 8.

With reference to FIG. 8A, a hardware configuration of the diagnosis support system 8 will be described. A CPU 8001 mainly controls operations by components. A main memory 8002 stores a control program to be executed by the CPU 8001 and provides work area for the execution of a program by the CPU 8001. A plurality of CPUs may be included. In that case, the plurality of CPUs may be distributed to implement the present invention. The control program stored in the main memory 8002 is software for implementing functions in FIG. 8B. A magnetic disk 8003 stores an operating system (OS), a device drive for a peripheral apparatus, and application software for including a program for executing processing, which will be described below. A display memory 8004 temporarily stores data for display. A monitor 8005 may be a CRT monitor or a liquid crystal monitor included in the display unit 804 in FIG. 8B and display an image and/or text on the basis of the data from the display memory 8004. A mouse 8006 and a keyboard 8007 are included in an operating unit 803 in FIG. 8B and are used for pointing input and character input by a user. The data server 8008 is included in a case information terminal 802 in FIG. 8B and stores a measured value relating to an image and/or tumor marker of a subject. These components are connected to each other via a common bus 8009 to communicate with each other.

FIG. 8B illustrates blocks of functions of the diagnosis support system 8 implemented by the hardware and software described above. The diagnosis support system 8 deduces the diagnosis of a subject on the basis of the information acquired from the case information terminal 802 and operating unit 803 by the diagnosis support apparatus 801. An input GUI which allows easy input of a finding through the operating unit 803 is displayed on the display unit 40. The deduction result is displayed on the display unit 804, and, among the findings, displays of a finding that affirms the deduction result most and a finding that denies it are given to input GUIs.

The display control unit 805 generates a subject image, measured values, impression and finding input GUIs, a deduction instruction button, and an image displaying a deduction result and displays them on the display unit 804. Among input findings, the display control unit 805 gives displays of a finding that affirms the deduction result and a finding against the deduction result to the finding input GUIs. In accordance with an operation signal by a user through the operating unit 803, input information is displayed in an input GUI, or the display disappears.

The medical information acquiring unit 806 acquires a finding input to an input GUI in response to the push of the deduction instruction button on the display unit 804. Measured values are acquired from the case information terminal 802.

The probability calculating unit 807 calculates the probability corresponding to a predetermined diagnosis on the basis of a finding and/or measured value, for example, acquired by the medical information acquiring unit 806. On the basis of the probability, the diagnosis calculating unit 808 deduces the diagnosis corresponding to the subject. A finding determining unit 809 uses the processing in the probability calculating unit 807 to determine the contribution ratios of findings regarding the deduced diagnosis and thus determine whether each of the findings affirms the deduction or not. The contribution ratio determination method may apply priori probabilities to the processing as in the first embodiment. The finding with a contribution ratio being the highest positive value is selected as a positive finding, and a the finding with a contribution ratio being the lowest negative value is selected as a negative finding. The display control unit 805 gives the displays that emphasize the positive finding and negative finding in accordance with the contribution ratios are given to the input GUIs through which the positive finding and negative finding are input.

The processing of the first embodiment may be implemented by storing a program for executing the processing illustrated in FIG. 4 to the main memory 8002. It also allows implementation of functions of the second and third embodiments.

In this way, the medical diagnosis support apparatus according to this embodiment sets a subject diagnosis from the deduction result based on input information through an input GUI and displays the subject diagnosis and the positive information and negative information for the diagnosis on the input GUIs with emphasis. This can provide a system that allows a user to check his or her input error and easily determine the reliability of the medical diagnosis support apparatus.

According to this embodiment, the present invention is applied to an image diagnosis support system. However, the present invention is applicable to diagnoses excluding the image diagnosis as in the case where a user facing a patient inputs a finding.

The processing to be performed in the diagnosis support apparatus may be distributed to a plurality of apparatuses to implement a diagnosis support system. Processes which can be merged to one functional block may be distributed to a plurality of circuits or function blocks for the implementation.

In another embodiment, the diagnose can only input one finding via the GUI 102, and the deducting unit 106 deduces the diagnosis of a subject on the basis of the finding and the associated clinical data such as a tumor marker value. If the deducting unit 106 determines that the input finding denies the result of the deduction, the emphasis display unit 112 performs display (emphasis display) which emphasizes the input GUI of the input finding.

Aspects of the present invention can also be realized by a computer of a system or apparatus (or devices such as a CPU or MPU) that reads out and executes a program recorded on a memory device to perform the functions of the above-described embodiment(s), and by a method, the steps of which are performed by a computer of a system or apparatus by, for example, reading out and executing a program recorded on a memory device to perform the functions of the above-described embodiment(s). For this purpose, the program is provided to the computer for example via a network or from a recording medium of various types serving as the memory device (e.g., computer-readable medium).

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-191212 filed Aug. 27, 2010, which is hereby incorporated by reference herein in its entirety.

What is claimed is:

1. A diagnosis support apparatus connected to a display unit and an operating unit, the diagnosis support apparatus comprising:
    a display control unit configured to cause the display unit to display a plurality of input graphical user interfaces (GUIs) into which a plurality of findings regarding a subject is to be input;
    an acquisition unit configured to acquire a deduction result of diagnosis for the subject by a deduction unit based on a plurality of findings input through the plurality of input GUIs in response to input from the operating unit;
    a processor configured to determine, as an effect of at least one input finding, a degree to which the input finding positively or negatively contributes to the diagnosis on the basis of a difference between a probability that the deducing unit deduces a predetermined diagnosis by using the input finding and a probability that the deducing unit deduces the predetermined diagnosis without using the input finding; and
    a selection unit configured to, based on the determined degree, select at least one finding from the plurality of input findings,
    wherein the display control unit is configured to cause the display unit to display the at least one finding input through at least one of the plurality of input GUIs and selected by the selection unit together with the plurality of input GUIs so that the at least one selected finding is distinguished from findings input through the at least one of the plurality of input GUIs and not selected by the selection unit.

2. The diagnosis support apparatus according to claim 1, wherein the display control unit is configured to cause the display unit to display the plurality of findings input through the plurality of input GUIs in association with the plurality of input GUIs, and configured to change a display form of an input GUI corresponding to the at least one selected finding.

3. The diagnosis support apparatus according to claim 1, wherein the display control unit is configured to cause the display unit to display the plurality of findings input through the plurality of input GUIs in association with the plurality of input GUIs and display an input GUI corresponding to the at least one selected finding with a marker.

4. The diagnosis support apparatus according to claim 1, wherein the display control unit is configured to cause the display unit to display the plurality of findings input through the plurality of input GUIs in association with the plurality of input GUIs, and configured to change a display attribute of an input GUI corresponding to the at least one finding input through at least one of the plurality of input GUIs and selected by the selection unit.

5. The diagnosis support apparatus according to claim 1, wherein the display control unit alters an appearance of an input GUI of a finding having a highest degree of support for the deduction result and an input GUI of a finding most negatively contributing to the deduction result.

6. The diagnosis support apparatus according to claim 1,
wherein the selection unit is configured to select at least one of diagnosis candidates as a selected diagnosis candidate, and
wherein the selection unit is configured to select the at least one of the plurality of input findings based on an influence on the selected diagnosis candidate by the at least one of the plurality of input findings.

7. The diagnosis support apparatus according to claim 1, wherein the display control unit is configured to change a display form of an input GUI corresponding to the at least one selected finding.

8. The diagnosis support apparatus according to claim 1, wherein the display control unit is configured to cause the display unit to display an input GUI corresponding to the at least one selected finding with a marker.

9. The diagnosis support apparatus according to claim 1, wherein the display control unit is configured to change a display attribute of an input GUI corresponding to the at least one finding input through at least one of the plurality of input GUIs and selected by the selection unit.

10. The diagnosis support apparatus according to claim 1, wherein the acquisition unit includes the deduction unit configured to deduce a diagnosis based on the plurality of findings input through the plurality of input GUIs in response to input from the operating unit and to acquire a deduction result for the subject.

11. The diagnosis support apparatus according to claim 10, wherein the deduction unit is configured to acquire a deduction result for the subject based on the plurality of findings input through the plurality of input GUIs in response to input from the operating unit and a measured value regarding the subject.

12. The diagnosis support apparatus according to claim 10, wherein the deduction unit is configured to calculate probabilities corresponding to diagnosis candidates for the subject and is configured to obtain, based on the calculated probabilities, at least one of the diagnosis candidates as the deduction result for the subject.

13. The diagnosis support apparatus according to claim 1, wherein the selection unit is configured to select at least one of a findings having a highest degree of support for the deduction result and a finding most negatively contributing to the deduction result.

14. A diagnosis support apparatus connected to a display unit and an operating unit, the diagnosis support apparatus comprising:
a display control unit configured to cause the display unit to display a plurality of input graphical user interfaces (GUIs) into which a plurality of findings regarding a subject is to be input;
an acquisition unit configured to acquire a deduction result of diagnosis for the subject by a deduction unit based on a plurality of findings input through the plurality of input GUIs in response to input from the operating unit;
a processor configured to determine, as an effect of at least one input finding, a degree to which the input finding positively or negatively contributes to the diagnosis on the basis of a difference between a probability that the deducing unit deduces a predetermined diagnosis by using the input finding and a probability that the deducing unit deduces the predetermined diagnosis without using the input finding; and
a selection unit configured to, based on an influence on the deduction result by the at least one input finding of the plurality of input findings, select at least one finding from the plurality of input findings,
wherein the display control unit is configured to cause the display unit to display an input GUI corresponding to the at least one select finding so that the input GUI is distinguished from input GUIs corresponding to findings not selected by the selection unit.

15. A diagnosis support system comprising:
a display unit;
an operating unit;
a display control unit configured to cause the display unit to display a plurality of input graphical user interfaces (GUIs) into which a plurality of findings regarding a subject is to be input;
a deduction unit configured to deduce a diagnosis and acquire a deduction result for the subject based on a plurality of findings input through the plurality of input GUIs in response to input from the operating unit;
a processor configured to determine, as an effect of at least one input finding, a degree to which the input finding positively or negatively contributes to the diagnosis on the basis of a difference between a probability that the deducing unit deduces a predetermined diagnosis by using the input finding and a probability that the deducing unit deduces the predetermined diagnosis without using the input finding; and
a selection unit configured to, based on an influence on the deduction result by the at least one input finding of the plurality of input findings, select at least one finding from the plurality of input findings,
wherein the display control unit is configured to cause the display unit to display the at least one finding input through at least one of the plurality of input GUIs and selected by the selection unit together with the plurality of input GUIs so that the at least one finding is distinguished from findings input through the at least one of the plurality of input GUIs and not selected by the selection unit.

16. A diagnosis support system comprising:
a display unit;
an operating unit;
a display control unit configured to cause the display unit to display a plurality of input graphical user interfaces (GUIs) into which a plurality of findings regarding a subject is to be input;
a deduction unit configured to deduce a diagnosis and acquire a deduction result for the subject based on a plurality of findings input through the plurality of input GUIs in response to input from the operating unit;
a processor configured to determine, as an effect of at least one input finding, a degree to which the input finding positively or negatively contributes to the diagnosis on the basis of a difference between a probability that the deducing unit deduces a predetermined diagnosis by using the input finding and a probability that the deducing unit deduces the predetermined diagnosis without using the input finding; and
a selection unit configured to, based on an influence on the deduction result by the at least one input finding of the plurality of input findings, select at least one finding from the plurality of input findings,
wherein the display control unit is configured to cause the display unit to display an input GUI corresponding to the at least one selected finding so that the input GUI is distinguished from input GUIs corresponding to findings not selected by the selection unit.

17. A method of operating a diagnosis support apparatus which includes a processor and is connected to a display unit and an operating unit, the method comprising:
causing the display unit to display a plurality of input graphical user interfaces (GUIs) into which a plurality of findings regarding a subject is to be input;
acquiring a deduction result of diagnosis for the subject based on a plurality of findings input through the plurality of input GUIs in response to input from the operating unit;
determining, using the processor, as an effect of at least one input finding, a degree to which the input finding positively or negatively contributes to the diagnosis on the basis of a difference between a probability that the deduction deduces a predetermined diagnosis by using the input finding and a probability that the deduction deduces the predetermined diagnosis without using the input finding; and
based on an influence on the deduction result by the at least one input finding of the plurality of input findings, selecting at least one finding from the plurality of input findings; and
causing the display unit to display the at least one finding input through at least one of the plurality of input GUIs and selected together with the plurality of input GUIs so that the at least one finding is distinguished from findings input through the at least one of the plurality of input GUIs and not selected.

18. The method according to claim 17, further comprising:
deducing a diagnosis based on the plurality of findings input through the plurality of input GUIs in response to input from the operating unit and acquiring a deduction result for the subject.

19. A non-transitory recording medium storing a program to cause a computer to execute the method according to claim 17.

20. A method of operating a diagnosis support apparatus which includes a processor and is connected to a display unit and an operating unit, the method comprising:
causing the display unit to display a plurality of input graphical user interfaces (GUIs) into which a plurality of findings regarding a subject is to be input;
acquiring a deduction result of deduction for the subject based on a plurality of findings input through the plurality of input GUIs in response to input from the operating unit;
determining, using the processor, as an effect of at least one input finding, a degree to which the input finding positively or negatively contributes to the diagnosis on the basis of a difference between a probability that the deducing unit deduces a predetermined diagnosis by using the input finding and a probability that the deduction result deduces the predetermined diagnosis without using the input finding; and
based on an influence on the deduction result by the at least one input finding of the plurality of input findings, selecting at least one finding from the plurality of input findings; and
causing the display unit to display an input GUI corresponding to the at least one selected finding so that the input GUI is distinguished from input GUIs corresponding to findings not selected.

21. The method according to claim 20, further comprising:
deducing a diagnosis based on the plurality of findings input through the plurality of input GUIs in response to input from the operating unit and acquiring a deduction result for the subject.

22. A non-transitory recording medium storing a program to cause a computer to execute the method according to claim 20.

23. A diagnosis support apparatus connected to a display unit and an operating unit, the diagnosis support apparatus comprising:
a display control unit configured to cause the display unit to display a plurality of input graphical user interfaces (GUIs) into which a plurality of findings regarding an object is to be input, wherein each of the findings includes a category and a state for the category, and a state for a category of a finding of the findings is to be input into the input GUI;
an acquisition unit configured to acquire a deduction result of diagnosis for the object by a deduction unit based on a plurality of findings input through the plurality of input GUIs in response to input from the operating unit;
a determination unit configured to determine an effect of a state of a finding on a deduction result of the diagnosis, based on the state; and
a selection unit configured to, based on the determined effect of at least one of states of the input findings on the acquired deduction result, select at least one of the input findings,
wherein the display control unit is configured to cause the display unit to display the at least one finding input through at least one of the plurality of input GUIs and selected by the selection unit together with the plurality of input GUIs so that the at least one selected finding is distinguished from findings input through the at least one of the plurality of input GUIs and not selected by the selection unit, wherein the determining unit is configured to determine, as the effect of the at least one finding, a degree that the input finding positively or negatively contributes to the diagnosis on the basis of a difference between a probability that the deducing unit deduces a predetermined diagnosis by using the input finding and a probability that the deducing unit deduces the predetermined diagnosis without using the finding.

* * * * *